US012642793B2

(12) United States Patent　　(10) Patent No.:　US 12,642,793 B2
Pimentel et al.　　(45) Date of Patent:　Jun. 2, 2026

(54) COMPOSITIONS AND METHODS TO TREAT GASTROINTESTINAL DISEASES AND DISORDERS

(71) Applicant: CEDARS-SINAI MEDICAL CENTER, Los Angeles, CA (US)

(72) Inventors: Mark Pimentel, Los Angeles, CA (US); Gabriela Guimaraes Sousa Leite, Los Angeles, CA (US); Ruchi Mathur, Los Angeles, CA (US); Ali Rezaie, West Hollywood, CA (US); Walter Morales, Rowland Heights, CA (US); Stacy Weitsman, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 915 days.

(21) Appl. No.: 17/440,427

(22) PCT Filed: Mar. 18, 2020

(86) PCT No.: PCT/US2020/023396
§ 371 (c)(1),
(2) Date: Sep. 17, 2021

(87) PCT Pub. No.: WO2020/191076
PCT Pub. Date: Sep. 24, 2020

(65) Prior Publication Data
US 2023/0038019 A1　　Feb. 9, 2023

Related U.S. Application Data

(60) Provisional application No. 62/819,986, filed on Mar. 18, 2019.

(51) Int. Cl.
| | |
|---|---|
| *A61K 31/437* | (2006.01) |
| *A61K 31/095* | (2006.01) |
| *A61K 31/197* | (2006.01) |
| *A61P 1/12* | (2006.01) |

(52) U.S. Cl.
CPC .......... *A61K 31/437* (2013.01); *A61K 31/095* (2013.01); *A61K 31/197* (2013.01); *A61P 1/12* (2018.01)

(58) Field of Classification Search
CPC .................................................... A61K 31/437
See application file for complete search history.

(56) References Cited

U.S. PATENT DOCUMENTS

| | | | |
|---|---|---|---|
| 3,847,973 A | 11/1974 | Vinals et al. |
| 6,599,885 B2 | 7/2003 | Schickaneder et al. |
| 6,805,852 B2 | 10/2004 | Lin et al. |
| 6,861,053 B1 | 3/2005 | Lin et al. |
| 7,056,686 B2 | 6/2006 | Lin et al. |
| 7,452,857 B2 | 11/2008 | Lin et al. |
| 7,585,838 B2 | 9/2009 | Lin et al. |
| 7,605,240 B2 | 10/2009 | Lin et al. |
| 7,718,608 B2 | 5/2010 | Lin et al. |
| 7,935,799 B2 | 5/2011 | Lin et al. |
| 8,197,805 B2 | 6/2012 | Lin et al. |
| 9,339,525 B2 | 5/2016 | O'Neil et al. |
| 9,364,491 B2 | 6/2016 | O'Neil et al. |
| 9,408,393 B2 | 8/2016 | Baker |
| 2006/0264409 A1 | 11/2006 | Harty |
| 2015/0024048 A1 | 1/2015 | Hemmingsen et al. |
| 2015/0290092 A1 | 10/2015 | Lee |
| 2017/0348253 A1 | 12/2017 | O'Neil et al. |
| 2017/0348360 A1 | 12/2017 | Borody |
| 2018/0071268 A1 | 3/2018 | Borody |
| 2019/0083518 A1 | 3/2019 | Borody et al. |
| 2022/0186281 A1 | 6/2022 | Leite et al. |
| 2025/0275950 A1 | 9/2025 | Pimentel et al. |

FOREIGN PATENT DOCUMENTS

| | | | | |
|---|---|---|---|---|
| EP | 0052910 A1 | 6/1982 | | |
| GB | 2091734 A | 8/1982 | | |
| MX | PA06014635 A | 11/2008 | | |
| WO | WO-2010072419 A2 * | 7/2010 | .............. | A61P 35/00 |
| WO | WO 2012/080700 A1 | 6/2012 | | |
| WO | WO 2014/032108 A1 | 3/2014 | | |
| WO | WO 2014/070769 A1 | 5/2014 | | |
| WO | 2014191410 A1 | 12/2014 | | |
| WO | 201513591 A1 | 1/2015 | | |
| WO | 2016003536 A1 | 1/2016 | | |
| WO | WO-2016174623 A1 * | 11/2016 | ........... | A61K 31/496 |
| WO | 2018148113 A1 | 8/2018 | | |
| WO | WO 2018-174839 A1 | 9/2018 | | |
| WO | WO 2018/189687 A1 | 10/2018 | | |

(Continued)

OTHER PUBLICATIONS

Sandberg (Townsend Letter—Feb./Mar. 20, 2015, https://sibocenter.com/wp-content/uploads/Dybiosis.pdf retrieved Jun. 20, 2024) (Year: 2015).*

Sandberg et. al. (Townsend Letter—Feb./Mar. 2015, p. 67-76) (Year: 2015).*

Gasberrini et. al. (Clinical Gastroenterology and Hepatology 2010;8:817â820) (Year: 2010).*

Charrier et al., "Cysteamine (Lynovex®), A Novel Mucoactive Antimicrobial & Antibiofilm Agent for the Treatment of Cystic Fibrosis," *Orphanet Journal of Rare Diseases*, vol. 9, No. 189, 11 pages, (2014).

Parry et al., "Effect of N-Acetylcysteine on Antibiotic Activity and Bacterial Growth In Vitro," *Journal of Clinical Microbiology*, vol. 5, No. 1, pp. 58-61, (1977).

Sezgin et al., "Addition of Rifaximin and N-Acetyl Cysteine to the Standard *Helicobacter pylori* Treatment Regimens: Is It Possible to Improve Outcomes?", *Journal of Gastric Disorders and Therapy*, vol. 2, No. 2, 5 pages, (2016).

(Continued)

*Primary Examiner* — John S Kenyon
*Assistant Examiner* — Rehana Ismail
(74) *Attorney, Agent, or Firm* — Linda B. Huber; Nixon Peabody LLP

(57) ABSTRACT

Described herein are compositions and methods of treating gastrointestinal diseases and disorders such as irritable bowel syndrome and small intestinal bacterial overgrowth.

12 Claims, No Drawings

(56)        References Cited

FOREIGN PATENT DOCUMENTS

| | | |
|---|---|---|
| WO | 2020191076 A1 | 9/2020 |
| WO | 2023225633 A1 | 11/2023 |

OTHER PUBLICATIONS

Valentina et al., "The Efficacy and Safety of Inhaled Fluimucil-antibiotic-IT in the Treatment of Exacerbations of COPD and Chronic Bronchitis with Bronchiectasis," *European Respiratory Society Annual Congress 2013*, 1 page, (2013) Abstract Only.

Dasaraju et al., "Chapter 93: Infections of the Respiratory System," *Medical Microbiology*, 4th Edition, 16 pages, (1996).

Highlights of Prescribing Information for Xifaxan® tablets, 20 pages (2004).

Irani, S., "Orofacial Bacterial Infectious Diseases: An Update," *J Int Soc Prev Community Dent.*, vol. 7, Suppl. No. 2, 12 pages (2017).

Sandberg-Lewis et al., "SIBO: Dysbiosis Has A New Name," *Best of Naturopathic Medicine*, 10 pages (2015).

Sicard et al., "Interactions of Intestinal Bacteria with Components of the Intestinal Mucus," *Frontiers in Cellular and Infection Microbiology*, vol. 7, No. 387, 12 pages (2017).

International Search Report and Written Opinion for PCT/US2020/23396, Jun. 9, 2020, 7 pages.

Salix Pharmaceuticals, Inc., Highlights of Prescribing Information, Xifaxan Rifaximin Tablets, 2015, retrieved from the internet: https://www.acessdata.fda.gov/drugsatfda_docs/label/2010/022554lbl.pdf.

Khamaneh et al., Combination of anti-tuberculosis drugs with vitamin C or NAC against different *Staphylococcus aureus* and *Mycobacterium* Tuberculossi strains, Microbial Pathogenesis 93, 2016, pp. 83-87.

Supplementary European Search Report for EP 20773187 dated Oct. 31, 2022.

Wang et al., Protective effects of N-acetylcysteine on acid-induced colitis in a porcine model, BMC Gastroenterology, 2013, vol. 13(1), p. 133.

Lazarova et al., The Antioxidant Acetylcysteine Reduces Oxidative Stress by Decreasing Level of Aopps, Biomed. Papers, 2004, vol. 148(2), pp. 131-133.

Yu et al., Protective effect of Nacetylcysteine on the murine model of ulcerative colitis induced by dextran sodium sulphate, Central South Pharmacy, 2007, vol. 5(4), pp. 296-299.

International Search Report and Written Opinion for PCT/US2023/067221, Sep. 21, 2023, 8 pages.

Leite et al., Tu1672 Rifaximin with N.Acetylcysteine (NAC) is superior to Rifaximin alone in a rat model of IBS-D: A Randomised Controlled Trial, Gastroenterology AGA Abstracts, 2024, vol. 166(5), pp. S-1373-S-1374.

Leite et al., Low dose rifaximin combined with N-acetylcysteine is superior to rifaximin alone in a rat model of IBS-D: a randomized trial, Scientific Reports, 2024, vol. 14, pp. 1-10.

* cited by examiner

COMPOSITIONS AND METHODS TO TREAT GASTROINTESTINAL DISEASES AND DISORDERS

CROSS-REFERENCE TO RELATED APPLICATIONS

This application is a U.S. National Stage Application under 35 U.S.C. § 371 of International Application No. PCT/US2020/023396, which was filed on Mar. 18, 2020, which claims the benefit of priority to U.S. Application No. 62/819,986, filed Mar. 18, 2019, the entirety of which is incorporated herein by reference.

FIELD OF THE INVENTION

This invention relates to pharmaceutical compositions and methods of treating gastrointestinal diseases and disorders including irritable bowel syndrome and small intestinal bacterial overgrowth.

BACKGROUND OF THE INVENTION

The mucus barrier has an important role in preventing infectious diseases. It provides protection against many intestinal pathogens, including various species of bacteria. Mucus is mainly formed of glycoproteins containing various glycans, but also contains a variety of nonspecific antimicrobial molecules and antibodies targeting specific microbial antigens. Mucus is therefore a major component of innate immunity, and generally prevents pathogens from reaching and persisting on epithelial surfaces within the body. However, some pathogens have evolved to adhere to mucus or to modulate the expression of virulence genes and thereby adapt to the host environment.

In the context of the gastrointestinal tract, an alteration of mucosal integrity is generally associated with health problems, such as inflammatory bowel diseases, including ulcerative colitis and Crohn's disease. Such changes in the mucosal environment could also be linked to dysbiosis, an abnormal change in the composition of the intestinal microbiota due to Crohn's disease. Once impaired, the mucus barrier becomes permeable to bacteria that are able to access the epithelium and therefore cause inflammation, which is why the integrity of the mucus layer is critical for the upkeep of a homeostatic relationship between the intestinal microbiota and its host.

Bacterial gastroenteritis is usually caused by eating contaminated food, drinking contaminated water, or close contact with an infected person. Bacterial toxins damage the cells lining the gastrointestinal tract, typically in the colon, resulting in diarrhea, watery stool and abdominal cramps, or dysentery (severe diarrhea, often accompanied by blood and mucus). Traveler's diarrhea is a common result of exposure to food or water containing pathogenic organisms to which the patient has not been previously exposed and therefore has an inadequate immune response. Bacterial enteropathogens include, e.g., enterotoxigenic *Escherichia coli* (ETEC), enteroaggregative *E. coli*, and various species of *Shigella, Salmonella, Campylobacter, Yersinia, Aeromonas*, and *Plesiomonas*. While most bacterial gastrointestinal illness is short-lived, severe diarrheal illness can lead to serious and sometimes fatal dehydration.

Irritable Bowel Syndrome (IBS) is the most common gastrointestinal disorder, with an estimated prevalence in the US of 10% to 15%. Estimates of the prevalence of IBS worldwide vary widely, due in part to differences in the diagnostic criteria used (Manning, Rome I, Rome II, Rome III) and a paucity of data from underdeveloped regions, but according to a meta-analysis by Lovell and Ford published in 2012, the pooled prevalence of IBS was 12.0% in Northern European studies, 15.0% in Southern European studies, 7.5% in Middle Eastern studies, 17% in South Asian studies, and 21% in South American studies. IBS is characterized by symptoms which include abdominal pain, bloating, and chronic changes in bowel function that may present as diarrhea-predominant (D-IBS), constipation-predominant (C-IBS) or alternate between the two (M-IBS). The cause of IBS is not fully understood. However, bacterial infections of the gastrointestinal tract have been linked with the occurrence of IBS. It is theorized that bacteria such as *Salmonella* spp. or *Campylobacter* spp. infiltrate the mucosal membrane of the small intestine, often resulting in increased incidence of lasting IBS symptoms.

Antibacterial agents often cannot penetrate the mucus layer adequately to control infections, but at the same time, the mucus layer provides an important protective role.

There is a need for improved treatment of conditions, diseases or disorders relating to bacterial infections of the gastrointestinal tract, such as bacterial gastroenteritis or irritable bowel syndrome.

SUMMARY OF THE INVENTION

A key step towards a more accurate understanding of the etiology of IBS was the recognition acute gastroenteritis could lead to the development of IBS. Approximately 10% of individuals who contract acute gastroenteritis go on to develop post-infectious IBS (PI-IBS), and it has since been shown that PI-IBS may be responsible for 9% or more of IBS cases. Different bacterial pathogens cause gastroenteritis and PI-IBS, of which *Campylobacter jejuni* is the most common in the US. *C. jejuni* and other pathogens that can cause PI-IBS all produce cytolethal distending toxin (Cdt), a heterotrimeric protein with three subunits, CdtA, CdtB, and CdtC. Of these. CdtB is the active toxin subunit and CdtA and CdtC are proposed to collaborate to facilitate the binding and entry of CdtB into mammalian cells. In early studies, rats infected with *C. jejuni* developed altered stool forms and other symptoms that resemble IBS in humans, whereas rats infected with a mutant form of *C. jejuni* that lacked CdtB did not. Rats directly injected with the CdtB toxin also developed increased bacterial levels in the small bowel, which further supported the hypothesis that CdtB was a key link between infection with pathogens like *C. jejuni* and the development of PI-IBS. In sum, food poisoning causes autoimmunity, which triggers neuropathy which triggers small intestinal bacterial overgrowth (SIBO), which leads to irritable bowel syndrome (IBS). Without being limited to any one theory, rifaximin is a treatment option for IBS and SIBO because it is not absorbed, or very minimally absorbed, into the body, and therefore has little to no side effects. Resistance does not appear to develop over repeated use.

In the gastrointestinal (GI) tract, mucus is protective, as it has components that protect the epithelium against pathogens and is also a natural barrier. However, some pathogens developed mechanisms to circumvent the protection or even use mucus to their advantage. For example, *C. jejuni, Salmonella, B. fragilis, C. difficile,* some strains of *E. coli,* and many other bacteria can adhere, survive and grow in mucus. Additionally, other non-pathogenic bacteria can also survive and grow in mucus including, *Bacteroides* sp and *Lactobacillus* sp (especially *reuteri* and *rhamnosus*).

Rifaximin is a minimally absorbed antibiotic that specifically targets the gastrointestinal tract and is FDA-approved for the treatment of IBS-D. Although treatment with rifaximin is extremely effective, symptom recurrence is common. The mucus layer in the small intestine is viscous, which can render the microbes in the mucus layer inaccessible. Without being limited to any one theory, this inaccessibility may protect certain bacterial species from the effects of rifaximin, thereby facilitating their regrowth and the recurrence of symptoms.

The reducing agent dithiothreitol (DTT) can reduce the disulfide bonds linking mucin subunits in mucus. For example, it may be used to reduce mucus viscosity. This led to the hypothesis that using rifaximin in combination with a mucolytic agent would make mucosal bacteria more accessible and thus improve the efficacy of rifaximin in treating IBS symptoms. DTT is not yet approved for use in humans, but the mucolytic agent N-acetylcysteine (NAC) is an approved agent.

Embodiments of the invention described herein include methods of treatment and combination products using an antibiotic, e.g., a rifamycin, such as rifaximin, and a mucolytic, e.g. NAC or DTT, wherein the mucolytic agent facilitates access for the antibiotic to a target microbe (e.g., pathogenic microbes, microbes that make up small intestinal bacterial overgrowth) by diluting the mucus in on the small intestine.

In an embodiment, the invention described herein includes a method for treating a condition, disease or disorder in a subject in need thereof. In some embodiments, the condition, disease or disorder may include a bacterial infection of the gastrointestinal tract. In some embodiments, the condition, disease, or disorder may be a gastrointestinal (GI) disease or disorder. In some embodiments, the GI disease or disorder may include small intestinal bacterial overgrowth (SIBO) or irritable bowel syndrome (IBS). In some embodiments, IBS may be diarrhea predominant irritable bowel syndrome (IBS-D), mixed irritable bowel syndrome (IBS-M), and constipation predominant irritable bowel syndrome (IBS-C). In an embodiment, the invention described herein may include a method for inhibiting the growth of or killing microorganisms in one or more regions of a subject's GI system. In an embodiment, the invention described herein may include a method of enhancing the efficacy of a rifamycin (e.g., rifaximin) against a condition, disease, or disorder involving a bacterial infection of the GI tract.

In some embodiments of the methods described herein, such methods may include the administration of a composition comprising a therapeutically effective amount of one or more antibiotics and a mucolytic agent.

In some embodiments of the methods described herein, such methods may include the administration of a therapeutically effective amount of one or more antibiotics and a mucolytic agent.

In some embodiments, the one or more antibiotics may include aminoglycosides (e.g., amikacin, gentamicin, kanamycin, neomycin, netilmicin, streptomycin, tobramycin, paromomycin), ansamycins (e.g., geldanamycin, herbimycin), carbacephems (e.g., loracarbef), carbapenems (e.g., ertapenem, doripenem, imipenem, cilastatin, meropenem), cephalosporins (e.g., first generation: cefadroxil, cefazolin, cefalotin or cefalothin, cefalexin; second generation: cefaclor, cefamandole, cefoxitin, cefprozil, cefuroxime; third generation: cefixime, cefdinir, cefditoren, cefoperazone, cefotaxime, cefpodoxime, ceftazidime, ceftibuten, ceftizoxime, ceftriaxone; fourth generation: cefepime; fifth generation: ceftobiprole), glycopeptides (e.g., teicoplanin, vancomycin), macrolides (e.g., azithromycin, clarithromycin, dirithromycin, erythromycin, roxithromycin, troleandomycin, telithromycin, spectinomycin), monobactams (e.g., aztreonam), penicillins (e.g., amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin), antibiotic polypeptides (e.g., bacitracin, colistin, polymyxin b), quinolones (e.g., ciprofloxacin, enoxacin, gatifloxacin, levofloxacin, lomefloxacin, moxifloxacin, norfloxacin, ofloxacin, trovafloxacin), rifamycins (e.g., rifampicin or rifampin, rifabutin, rifapentine, rifaximin), sulfonamides (e.g., mafenide, prontosil, sulfacetamide, sulfamethizole, sulfanilamide, sulfasalazine, sulfisoxazole, trimethoprim, trimethoprim-sulfamethoxazole (co-trimoxazole, "tmp-smx"), and tetracyclines (e.g., demeclocycline, doxycycline, minocycline, oxytetracycline, tetracycline) as well as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin combination, and tinidazole.

In some embodiments, the one or more antibiotics may include a rifamycin. In some embodiments, the rifamycin may be selected from the group consisting of rifampicin, rifampin, rifabutin, rifapentine, and rifaximin. In some embodiments, the one or more antibiotics may be selected from the group consisting of a rifaximin, rifamycin, rifampin, penicillin derivative, fluoroquinolone, macrolide, tetracycline, doxycycline, neomycin, and metronidazole. In some embodiments, the one or more antibiotics may include rifaximin. In some embodiments, the one or more antibiotics include rifaximin and neomycin.

In some embodiments, the rifamycin may be administered in a dosage of about 25 mg to about 1000 mg. In some embodiments, the rifamycin is rifaximin and may be administered in a dosage of about 550 mg, 500 mg, 400 mg, 350 mg, 300 mg, 275 mg. 250 mg, 225 mg, 200 mg, 175 mg, 150 mg, 125 mg, 100 mg, 75 mg, 50 mg or 25 mg; or greater than about 550 mg, 500 mg, 400 mg, 350 mg, 300 mg, 275 mg, 250 mg, 225 mg, 200 mg, 175 mg, 150 mg, 125 mg, 100 mg, 75 mg. 50 mg or 25 mg; or less than about 550 mg, 500 mg, 400 mg, 350 mg, 300 mg, 275 mg, 250 mg, 225 mg, 200 mg, 175 mg, 150 mg, 125 mg, 100 mg, 75 mg, 50 mg or 25 mg.

In some embodiments, the mucolytic agent may be selected from the group consisting of selected from the group consisting of dithiothreitol (DTT), N-acetyl cysteine (NAC), acetylcysteine, ambroxol, bromhexine, carbocisteine, erdosteine, mecysteine, and dornase alfa. In some embodiments, the mucolytic agent may be DTT or NAC. In some embodiments, the mucolytic agent is NAC. In some embodiments, the mucolytic agent is administered in an amount of about 100 mg to 1200 mg. In some embodiments, the mucolytic agent is NAC, which may be administered in an amount of about 100, 200, 300, 400, 500, 600, 700, 800, 900, 1000, 1100, or 1200 mg; or greater than about 100, 200, 300, 400, 500, 600, 700, 800, 900, 1000, 1100, or 1200 mg; or less than about 100, 200, 300, 400, 500, 600, 700, 800, 900, 1000, 1100, or 1200 mg.

In some embodiments, the one or more antibiotics and mucolytic agent may be administered as one composition or they may be administered as separate compositions in accordance with the methods described herein.

In accordance with the embodiments described herein, the combination of a mucolytic agent (e.g., NAC) with one or more antibiotics (e.g., rifaximin), either in the form of a single composition or separately administered, results in increased therapeutic efficacy for the one or more antibiotics and thus a reduced dosage may be provided as compared to the one or more antibiotics alone. Furthermore, a mucolytic agent, combined with an antibiotic, may increase the solubility of the antibiotic described herein as compared to the antibiotic alone.

DETAILED DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3rd ed., *Revised*, J. Wiley & Sons (New York, NY 2006); March, *Advanced Organic Chemistry Reactions, Mechanisms and Structure* 7th ed., J. Wiley & Sons (New York, NY 2013); and Sambrook and Russel, *Molecular Cloning: A Laboratory Manual* 4th ed., Cold Spring Harbor Laboratory Press (Cold Spring Harbor, NY 2012), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

Compositions

Various embodiments of the invention provide for a composition comprising: one or more antibiotics; and a mucolytic agent.

Examples of antibiotics that can be included in the composition include but are not limited to aminoglycosides (e.g., amikacin, gentamicin, kanamycin, neomycin, netilmicin, streptomycin, tobramycin, paromomycin), ansamycins (e.g., geldanamycin, herbimycin), carbacephems (e.g., loracarbef), carbapenems (e.g., ertapenem, doripenem, impenem, cilastatin, meropenem), cephalosporins (e.g., first generation: cefadroxil, cefazolin, cefalotin or cefalothin, cefalexin; second generation: cefaclor, cefamandole, cefoxitin, cefprozil, cefuroxime; third generation: cefixime, cefdinir, cefditoren, cefoperazone, cefotaxime, cefpodoxime, ceftazidime, ceftibuten, ceftizoxime, ceftriaxone; fourth generation: cefepime; fifth generation: ceftobiprole), glycopeptides (e.g., teicoplanin, vancomycin), macrolides (e.g., azithromycin, clarithromycin, dirithromycin, erythromycin, roxithromycin, troleandomycin, telithromycin, spectinomycin), monobactams (e.g., aztreonam), penicillins (e.g., amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin), antibiotic polypeptides (e.g., bacitracin, colistin, polymyxin b), quinolones (e.g., ciprofloxacin, enoxacin, gatifloxacin, levofloxacin, lomefloxacin, moxifloxacin, norfloxacin, ofloxacin, trovafloxacin), rifamycins (e.g., rifampicin or rifampin, rifabutin, rifapentine, rifaximin), sulfonamides (e.g., mafenide, prontosil, sulfacetamide, sulfamethizole, sulfanilamide, sulfasalazine, sulfisoxazole, trimethoprim, trimethoprim-sulfamethoxazole (co-trimoxazole, "tmp-smx"), and tetracyclines (e.g., demeclocycline, doxycycline, minocycline, oxytetracycline, tetracycline) as well as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin combination, and tinidazole.

In various embodiments, the one or more antibiotics is selected from the group consisting of rifaximin, rifamycin, rifampin, penicillin derivative, fluoroquinolone, macrolide, tetracycline, doxycycline, neomycin, metronidazole and combinations thereof. In various embodiments, the penicillin derivative is ampicillin, the fluoroquinolone is ciprofloxacin, and the macrolide is azithromycin. In various embodiments, the one or more antibiotics includes rifaximin. In various embodiments, the one or more antibiotics includes rifaximin and neomycin.

In various embodiments, the one or more antibiotics is rifaximin and the composition comprises 550 mg, 500 mg, 400 mg, 350 mg, 300 mg. 275 mg. 250 mg, 225 mg. 200 mg. 175 mg, 150 mg, 125 mg, 100 mg, 75 mg, 50 mg or 25 mg of rifaximin. In some embodiments, the one or more antibiotic is rifaximin and the composition comprises less than about 550 mg, 500 mg, 400 mg, 350 mg, 300 mg, 275 mg, 250 mg, 225 mg, 200 mg, 175 mg, 150 mg, 125 mg, 100 mg, 75 mg, 50 mg or 25 mg of rifaximin. In some embodiments, the one or more antibiotic is rifaximin and the composition comprises greater than about 550 mg, 500 mg, 400 mg, 350 mg, 300 mg. 275 mg, 250 mg, 225 mg, 200 mg, 175 mg, 150 mg, 125 mg, 100 mg, 75 mg, 50 mg or 25 mg of rifaximin.

The currently approved dose of rifaximin to treat diarrhea predominant IBS is 550 mg. While not wishing to be bound by any particular theory, the combination of an antibiotic and a mucolytic agent is believed to vastly increases therapeutic efficacy, and thus, the amount of the antibiotic can be reduced significantly. In some embodiments, a therapeutically effective dose of rifaximin (in combination with a mucolytic agent, e.g., NAC or DTT) in the invention described herein may be a dose that has increased activity in a subject as compared to the same dose of rifaximin provided to a subject without combination with a mucolytic agent (e.g., NAC or DTT). In some embodiments, the increased activity may be greater than about a 10%, 25%, 50%, 75%, 100%, 125%, 150%, 175%, 200%, 225%, 250%, 275%, 300%, 325%, 350%, 375%, 400%, 425%. 450%, 475%, or 500% increase in activity for a rifaximin dosage combined with a mucolytic agent as compared to the same rifaximin dosage without such combination. In some embodiments, the increased activity may be less than about a 10%, 25%, 50%, 75%, 100%, 125%, 150%, 175%, 200%, 225%, 250%, 275%, 300%, 325%, 350%, 375%, 400%, 425%, 450%, 475%, or 500% increase in activity for a rifaximin dosage combined with a mucolytic agent as compared to the same rifaximin dosage without such combination. In some embodiments, the increased activity may be about a 10%, 25%, 50%, 75%, 100%, 125%, 150%, 175%, 200%, 225%, 250%, 275%, 300%, 325%, 350%, 375%, 400%, 425%, 450%, 475%, or 500% increase in activity for a rifaximin dosage combined with a mucolytic agent as compared to the same rifaximin dosage without such combination.

Thus, in various embodiments wherein the one or more antibiotics is rifaximin, the composition comprises 250 mg. 225 mg. 200 mg, 175 mg, 150 mg, 125 mg, 100 mg, 75 mg, 50 mg or 25 mg of rifaximin. In some embodiments, the composition comprises greater than about 250 mg, 225 mg, 200 mg, 175 mg, 150 mg, 125 mg, 100 mg, 75 mg, 50 mg or 25 mg of rifaximin. In some embodiments, the composition comprises less than about 250 mg. 225 mg, 200 mg, 175 mg, 150 mg, 125 mg, 100 mg, 75 mg, 50 mg or 25 mg of rifaximin.

An approved dosage of rifaximin is 200 mg for the treatment of Travelers' diarrhea. While not wishing to be bound by any particular theory, the inventor believes that dosages lower than 200 mg can be effective in light of the increased therapeutic efficacy when combined or administered with a mucolytic agent. Thus, in various embodiments wherein the one or more antibiotic is rifaximin, the composition comprises 175 mg, 150 mg, 125 mg, 100 mg, 75 mg, 50 mg or 25 mg of rifaximin.

In various embodiments, the one or more antibiotics is rifaximin and neomycin. In various embodiments, the quantity of rifaximin is 550 mg, 500 mg, 400 mg, 350 mg, 300 mg, 275 mg, 250 mg, 225 mg, 200 mg, 175 mg, 150 mg, 125 mg, 100 mg, 75 mg, 50 mg or 25 mg, and the quantity of neomycin is 500 mg, 500 mg, 400 mg, 350 mg, 300 mg, 275 mg, 250 mg, 225 mg, 200 mg, 175 mg, 150 mg, 125 mg, 100 mg, 75 mg, 50 mg or 25 mg. In some embodiments, the quantity of rifaximin is less than about 550 mg, 500 mg, 400 mg, 350 mg, 300 mg, 275 mg, 250 mg. 225 mg, 200 mg, 175 mg, 150 mg, 125 mg, 100 mg, 75 mg, 50 mg or 25 mg, and the quantity of neomycin is less than about 500 mg, 500 mg, 400 mg, 350 mg, 300 mg. 275 mg, 250 mg, 225 mg, 200 mg, 175 mg, 150 mg, 125 mg, 100 mg, 75 mg, 50 mg or 25 mg. In some embodiments, the quantity of rifaximin is greater than about 550 mg, 500 mg, 400 mg, 350 mg, 300 mg. 275 mg, 250 mg, 225 mg, 200 mg, 175 mg, 150 mg, 125 mg, 100 mg, 75 mg, 50 mg or 25 mg, and the quantity of neomycin is greater than about 500 mg, 500 mg, 400 mg, 350 mg, 300 mg. 275 mg, 250 mg, 225 mg, 200 mg, 175 mg, 150 mg, 125 mg, 100 mg, 75 mg, 50 mg or 25 mg.

As noted above, the combination of an antibiotic and a mucolytic agent provides vastly increased therapeutic efficacy, and thus, the amount of the antibiotic(s) can be reduced significantly. Thus, in various embodiments wherein the one or more antibiotic is rifaximin and neomycin, the quantity of rifaximin is 250 mg. 225 mg, 200 mg, 175 mg, 150 mg, 125 mg, 100 mg, 75 mg, 50 mg or 25 mg, and quantity of neomycin is 250 mg, 225 mg, 200 mg, 175 mg, 150 mg, 125 mg, 100 mg, 75 mg, 50 mg or 25 mg. In some embodiments, the quantity of rifaximin is greater than about 250 mg. 225 mg, 200 mg, 175 mg, 150 mg, 125 mg, 100 mg. 75 mg, 50 mg or 25 mg, and quantity of neomycin is greater than about 250 mg. 225 mg. 200 mg, 175 mg, 150 mg, 125 mg, 100 mg. 75 mg, 50 mg or 25 mg. In some embodiments, the quantity of rifaximin is less than about 250 mg, 225 mg. 200 mg, 175 mg, 150 mg, 125 mg, 100 mg, 75 mg, 50 mg or 25 mg, and quantity of neomycin is less than about 250 mg. 225 mg. 200 mg, 175 mg, 150 mg, 125 mg, 100 mg, 75 mg, 50 mg or 25 mg.

In various embodiments wherein the one or more antibiotic is rifaximin and neomycin, the quantity of rifaximin is 175 mg, 150 mg, 125 mg, 100 mg, 75 mg, 50 mg or 25 mg, and quantity of neomycin is 250 mg. 225 mg, 200 mg, 175 mg, 150 mg, 125 mg, 100 mg, 75 mg, 50 mg or 25 mg.

In various embodiments, the mucolytic agent is selected from the group consisting of dithiothreitol (DTT), N-acetyl cysteine (NAC), acetylcysteine, ambroxol, bromhexine, carbocisteine, erdosteine, mecysteine, dornase alfa and combinations thereof. In some embodiments, the mucolytic agent is selected from the group consisting of dithiothreitol (DTT) and N-acetyl cysteine (NAC). In various embodiments, the mucolytic agent is dithiothreitol (DTT). In various embodiments, the mucolytic agent is N-acetyl cysteine (NAC).

In embodiments wherein the mucolytic agent is dithiothreitol (DTT), the composition comprises 10-20 v/v % of DTT. In various embodiments wherein the mucolytic agent is dithiothreitol (DTT), the composition comprises 5, 10, 15, 20 or 25 v/v % of DTT. In various embodiments wherein the mucolytic agent is dithiothreitol (DTT), the composition comprises greater than about 5, 10, 15, 20 or 25 v/v % of DTT. In various embodiments wherein the mucolytic agent is dithiothreitol (DTT), the composition comprises less than about 5, 10, 15, 20 or 25 v/v % of DTT. In various embodiments wherein the mucolytic agent is dithiothreitol (DTT), the composition comprises 10, 11, 12, 13, 14, 15, 16, 17, 18, 19 or 20 v/v % of DTT. DTT is available, for example, as a 6.5 mM solution in 100 mM phosphate buffer (pH 7).

In embodiments wherein mucolytic agent is N-acetyl cysteine (NAC), the composition comprises 100-1200 mg of N-acetyl cysteine (NAC). In various embodiments wherein mucolytic agent is N-acetyl cysteine (NAC), the composition comprises 50-100 mg, 100-200 mg, 200-300 mg, 300-400 mg, 400-500 mg, 500-600 mg. 600-700 mg. 700-800 mg. 800-900 mg, 900-1000 mg, 1000-1100 mg, 1100-1200 mg, 1200-1300 mg, 1300-1400 mg, or 1400-1500 mg of N-acetyl cysteine (NAC) per dose. In various embodiments wherein mucolytic agent is N-acetyl cysteine (NAC), the composition comprises 100, 200, 300, 400, 500, 600, 700, 800, 900, 1000, 1100, or 1200 mg of N-acetyl cysteine (NAC) per dose. In various embodiments wherein mucolytic agent is N-acetyl cysteine (NAC), the composition comprises greater than about 100, 200, 300, 400, 500, 600, 700, 800, 900, 1000, 1100, or 1200 mg of N-acetyl cysteine (NAC) per dose. In various embodiments wherein mucolytic agent is N-acetyl cysteine (NAC), the composition comprises less than about 100, 200, 300, 400, 500, 600, 700, 800, 900, 1000, 1100, or 1200 mg of N-acetyl cysteine (NAC) per dose.

In various embodiments, the invention described herein provides pharmaceutical compositions including a pharmaceutically acceptable excipient along with a therapeutically effective amount of the one or more antibiotics and mucolytic agent (as one composition or as separate compositions). "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In certain embodiments, the compounds of the invention described herein may contain one or more acidic functional groups and, thus, are capable of forming pharmaceutically acceptable salts with pharmaceutically acceptable bases. The term "pharmaceutically acceptable salts, esters, amides, and prodrugs" as used herein refers to those carboxylate salts, amino acid addition salts, esters, amides, and prodrugs of the compounds of the invention described herein which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the invention described herein. These salts can be prepared in situ during the final isolation and purification of the compounds or by separately reacting the purified compound in its free base form with a suitable organic or inorganic acid and isolating the salt thus formed. These may include cations based on the alkali and alkaline earth metals such as sodium, lithium, potassium, calcium, magnesium and the like, as well as nontoxic ammonium, quaternary ammonium, and amine cations including, but not limited to ammonium, tetramethylanunonium, tetraethyl ammonium, methyl amine, dimethyl amine, trimethylamine, triethylamine, ethylamine, and the like.

The term "pharmaceutically acceptable esters" refers to the relatively nontoxic, esterified products of the compounds of the invention described herein. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

As used herein, "pharmaceutically acceptable salts or prodrugs" are salts or prodrugs that are, within the scope of sound medical judgment, suitable for use in contact with the tissues of subject without undue toxicity, irritation, allergic response, and the like, commensurate with a reasonable benefit/risk ratio, and effective for their intended use.

The term "prodrug" refers to compounds that are rapidly transformed in vivo to yield the functionally active compounds disclosed herein. As used herein, a prodrug is a compound that, upon in vivo administration, is metabolized or otherwise converted to the biologically, pharmaceutically or therapeutically active form of the compound. A prodrug of the one or more antibiotics as disclosed herein can be designed to alter the metabolic stability or the transport characteristics of one or more antibiotics as disclosed herein, to mask side effects or toxicity, to improve the flavor of a compound or to alter other characteristics or properties of a compound. Suitable examples of prodrugs include methyl, ethyl and glycerol esters of the corresponding acid.

Methods of Treatment

In an embodiment, the invention described herein includes methods for treating a gastrointestinal (GI) disease or disorder. Various embodiments provide for a method of treating a gastrointestinal (GI) disease or disorder, comprising administering the composition comprising one or more antibiotics and a mucolytic agent. Various embodiments provide for a method of treating a gastrointestinal (GI) disease or disorder, comprising administering one or more antibiotics and administering a mucolytic agent.

In some embodiments, the GI disease or disorder is selected from the group consisting of small intestinal bacterial overgrowth (SIBO) or irritable bowel syndrome (IBS). In some embodiments, irritable bowel syndrome (IBS) is selected from the group consisting of diarrhea predominant irritable bowel syndrome (IBS-D), mixed irritable bowel syndrome (IBS-M), and constipation predominant irritable bowel syndrome (IBS-C).

In an embodiment, the invention described herein includes methods for inhibiting the growth of or killing microorganisms in one or more regions of a subject's gastrointestinal (GI) system. Various embodiments of the invention provide for a method of inhibiting the growth of or killing microorganisms in one or more regions of a subject's gastrointestinal (GI) system, comprising: administering the composition comprising one or more antibiotics and a mucolytic agent. Various embodiments of the invention provide for a method of inhibiting the growth of or killing microorganisms in one or more regions of a subject's gastrointestinal (GI) system, comprising: administering one or more antibiotics and administering a mucolytic agent. In various embodiments, the one or more regions of the subject's GI system is the small intestines. In various embodiments, the one or more regions of the subject's GI system is the esophagus, stomach, or colon.

In various embodiments, the microorganism is selected from the group consisting of *Proteus, Citrobacter, Aeromonas, Klebsiella, Methanobrevibacter, Eshericia, Salmonella, Lactobacillus, Disulfovibrio, Campylobacter, Bacteroides, Fusobacterium, Bilophila, Shigella, Moraxella, Morganella, Serratia, Enterobacter, Pseudomonas, Acinetobacter, Streptococcus, Veillonella, Prevotella, Paraprevotell, Rothia, Enterobacter, Providencia, Sutterella, Corpococcus, Lachnospira, Roseburia* and combinations thereof.

In various embodiments, the microorganism is selected from the group consisting of *C. jejuni, Salmonella, B. fragilis, C. difficile, E. coli, Bacteroides* sp, *Lactobacillus* sp (e.g., *reuteri* and *rhamnosus*), and combinations thereof.

In some embodiments, the methods described herein may include administering a composition comprising one or more antibiotics and a mucolytic agent. In some embodiments, the methods described herein may include administering one or more antibiotics and a mucolytic agent.

In various embodiments, the composition comprising one or more antibiotics and the mucolytic agent is administered for about 1 week, 2 weeks, 3 weeks. In various embodiments, the composition comprising one or more antibiotics and the mucolytic agent is administered for about 3, 4, 5, 6, 7, 8, 9, 10, 11, 12, 13, 14, or 15 days. In various embodiments, the composition is administered for about 1, 2, 3 or 4 times per day. In various embodiments, the composition is administered for about 1 or 2 or 3 times per day.

In various embodiments, the one or more antibiotics and the mucolytic agent are administered for about 1 week, 2 weeks, 3 weeks. In various embodiments, the one or more antibiotics and the mucolytic agent are administered for about 3, 4, 5, 6, 7, 8, 9, 10, 11, 12, 13, 14, or 15 days. In various embodiments, the one or more antibiotics and the mucolytic agent are administered for about 1, 2, 3, or 4 times per day. In various embodiments, the one or more antibiotics and the mucolytic agent are administered for about 1 or 2 or 3 times per day.

Examples of antibiotics are as noted above.

In various embodiments, the one or more antibiotics is selected from the group consisting of rifaximin, rifamycin, rifampin, penicillin derivative, fluoroquinolone, macrolide, tetracycline, doxycycline, neomycin, metronidazole and combinations thereof. In various embodiments, wherein the penicillin derivative is ampicillin, the fluoroquinolone is ciprofloxacin, and the macrolide is azithromycin. In various embodiments, the one or more antibiotics is rifaximin. In various embodiments, the one or more antibiotics is rifaximin and neomycin.

In various embodiments, the one or more antibiotic is rifaximin and the quantity of rifaximin is 550 mg, 500 mg, 400 mg, 350 mg, 300 mg, 275 mg, 250 mg, 225 mg, 200 mg, 175 mg, 150 mg, 125 mg, 100 mg, 75 mg, 50 mg or 25 mg. In some embodiments, the one or more antibiotic is rifaximin and the quantity of rifaximin less than about 550 mg, 500 mg, 400 mg, 350 mg, 300 mg, 275 mg, 250 mg, 225 mg, 200 mg, 175 mg, 150 mg, 125 mg, 100 mg, 75 mg, 50 mg or 25 mg. In some embodiments, the one or more antibiotic is rifaximin and the quantity of rifaximin greater than about 550 mg, 500 mg, 400 mg, 350 mg, 300 mg, 275 mg, 250 mg, 225 mg, 200 mg, 175 mg, 150 mg, 125 mg, 100 mg, 75 mg, 50 mg or 25 mg.

As noted above, the combination of an antibiotic and a mucolytic agent provides vastly increased therapeutic efficacy, and thus, the amount of the antibiotic can be reduced significantly. Thus, in various embodiments wherein the one or more antibiotic is rifaximin, the quantity of rifaximin is 250 mg. 225 mg, 200 mg, 175 mg, 150 mg, 125 mg, 100 mg, 75 mg, 50 mg or 25 mg. In various embodiments wherein the one or more antibiotic is rifaximin the quantity of rifaximin is 175 mg, 150 mg, 125 mg, 100 mg, 75 mg, 50 mg or 25 mg. In some embodiments, the quantity of rifaximin is greater than about 250 mg. 225 mg, 200 mg, 175 mg, 150 mg, 125 mg, 100 mg, 75 mg, 50 mg or 25 mg. In some embodiments, the quantity of rifaximin is less than about 250 mg, 225 mg, 200 mg, 175 mg, 150 mg, 125 mg, 100 mg, 75 mg, 50 mg or 25 mg.

In various embodiments, the one or more antibiotics is rifaximin and neomycin. In various embodiments, the quantity of rifaximin is 550 mg, 500 mg, 400 mg, 350 mg, 300 mg, 275 mg, 250 mg, 225 mg, 200 mg, 175 mg, 150 mg, 125 mg, 100 mg, 75 mg, 50 mg or 25 mg, and the quantity of neomycin is 500 mg, 500 mg, 400 mg, 350 mg, 300 mg, 275 mg, 250 mg, 225 mg, 200 mg, 175 mg, 150 mg, 125 mg, 100 mg, 75 mg, 50 mg or 25 mg. In some embodiments, the quantity of rifaximin is greater than about 550 mg, 500 mg, 400 mg, 350 mg, 300 mg, 275 mg, 250 mg, 225 mg. 200 mg, 175 mg, 150 mg, 125 mg, 100 mg, 75 mg, 50 mg or 25 mg, and the quantity of neomycin is greater than about 500 mg, 500 mg, 400 mg, 350 mg, 300 mg, 275 mg, 250 mg, 225 mg, 200 mg, 175 mg, 150 mg, 125 mg, 100 mg, 75 mg, 50 mg or 25 mg. In some embodiments, the quantity of rifaximin is less than about 550 mg, 500 mg, 400 mg, 350 mg, 300 mg, 275 mg, 250 mg, 225 mg, 200 mg, 175 mg, 150 mg, 125 mg, 100 mg. 75 mg, 50 mg or 25 mg, and the quantity of neomycin is less than about 500 mg, 500 mg, 400 mg, 350 mg, 300 mg, 275 mg, 250 mg. 225 mg, 200 mg, 175 mg, 150 mg, 125 mg, 100 mg, 75 mg, 50 mg or 25 mg.

As noted above, the combination of an antibiotic and a mucolytic agent provides vastly increased therapeutic efficacy, and thus, the amount of the antibiotic(s) can be reduced significantly. Thus, in various embodiments wherein the one or more antibiotic is rifaximin and neomycin, the quantity of rifaximin is 250 mg, 225 mg, 200 mg, 175 mg, 150 mg, 125 mg, 100 mg, 75 mg, 50 mg or 25 mg, and quantity of neomycin is 250 mg, 225 mg, 200 mg, 175 mg, 150 mg, 125 mg, 100 mg, 75 mg, 50 mg or 25 mg. In some embodiments, the quantity of rifaximin is greater than about 250 mg, 225 mg, 200 mg, 175 mg, 150 mg, 125 mg, 100 mg, 75 mg, 50 mg or 25 mg, and quantity of neomycin is greater than about 250 mg, 225 mg, 200 mg, 175 mg, 150 mg, 125 mg, 100 mg, 75 mg, 50 mg or 25 mg. In some embodiments, the quantity of rifaximin is less than about 250 mg, 225 mg. 200 mg, 175 mg, 150 mg, 125 mg, 100 mg. 75 mg, 50 mg or 25 mg, and quantity of neomycin is less than about 250 mg. 225 mg, 200 mg, 175 mg, 150 mg, 125 mg, 100 mg, 75 mg, 50 mg or 25 mg.

In various embodiments wherein the one or more antibiotic is rifaximin and neomycin, the quantity of rifaximin is 175 mg, 150 mg, 125 mg, 100 mg, 75 mg, 50 mg or 25 mg, and quantity of neomycin is 250 mg. 225 mg. 200 mg, 175 mg, 150 mg, 125 mg, 100 mg. 75 mg, 50 mg or 25 mg.

In various embodiments, the mucolytic agent is selected from the group consisting of dithiothreitol (DTT), N-acetyl cysteine (NAC), acetylcysteine, ambroxol, bromhexine, carbocisteine, erdosteine, mecysteine, dornase alfa and combinations thereof. In various embodiments, the mucolytic agent is dithiothreitol (DTT). In various embodiments, the mucolytic agent is N-acetyl cysteine (NAC).

In embodiments wherein the mucolytic agent is dithiothreitol (DTT), the DTT may be administered via a composition that comprises 10-20 v/v % of DTT. In various embodiments wherein the mucolytic agent is dithiothreitol (DTT), the DTT may be administered via a composition that comprises 5, 10, 15, 20 or 25 v/v % of DTT. In various embodiments wherein the mucolytic agent is dithiothreitol (DTT), the DTT may be administered via a composition that comprises greater than about 5, 10, 15, 20 or 25 v/v % of DTT. In various embodiments wherein the mucolytic agent is dithiothreitol (DTT), the DTT may be administered via a composition that comprises less than about 5, 10, 15, 20 or 25 v/v % of DTT. In various embodiments wherein the mucolytic agent is dithiothreitol (DTT), the DTT may be administered via a composition that comprises 10, 11, 12, 13, 14, 15, 16, 17, 18, 19 or 20 v/v % of DTT.

In embodiments wherein mucolytic agent is N-acetyl cysteine (NAC), the NAC may be administered via a composition that comprises 100-1200 mg of N-acetyl cysteine (NAC). In various embodiments wherein mucolytic agent is N-acetyl cysteine (NAC), the NAC may be administered via a composition that comprises 50-100 mg, 100-200 mg, 200-300 mg, 300-400 mg, 400-500 mg, 500-600 mg, 600-700 mg. 700-800 mg, 800-900 mg. 900-1000 mg, 1000-1100 mg, 1100-1200 mg, 1200-1300 mg, 1300-1400 mg, or 1400-1500 mg of N-acetyl cysteine (NAC) per dose. In various embodiments wherein mucolytic agent is N-acetyl cysteine (NAC), the NAC may be administered via a composition that comprises 100, 200, 300, 400, 500, 600, 700, 800, 900, 1000, 1100, or 1200 mg of N-acetyl cysteine (NAC) per dose. In various embodiments wherein mucolytic agent is N-acetyl cysteine (NAC), the NAC may be administered via a composition that comprises greater than about 100, 200, 300, 400, 500, 600, 700, 800, 900, 1000, 1100, or 1200 mg of N-acetyl cysteine (NAC) per dose. In various embodiments wherein mucolytic agent is N-acetyl cysteine (NAC), the NAC may be administered via a composition that comprises less than about 100, 200, 300, 400, 500, 600, 700, 800, 900, 1000, 1100, or 1200 mg of N-acetyl cysteine (NAC) per dose.

In various embodiments, the mucolytic agent dosage may be administered in one unit of a dosage form (e.g., one tablet). In some embodiments, the mucolytic agent dosage may be administered in two or more units of a dosage form (e.g., two, three, four, five, six, or more tablets).

In various embodiments, the GI disease or disorder is small intestinal bacterial overgrowth (SIBO).

In various embodiments, the GI disease or disorder is irritable bowel syndrome (IBS).

In various embodiments, the GI disease or disorder is diarrhea predominant irritable bowel syndrome (IBS-D). In various embodiments wherein the GI disease or disorder is IBS-D, the one or more antibiotics is rifaximin, which may be administered according to a quantity as set forth herein. In various embodiments, the quantity of rifaximin is 550 mg, 500 mg, 400 mg, 350 mg. 300 mg, 275 mg, 250 mg, 225 mg, 200 mg, 175 mg, 150 mg, 125 mg, 100 mg, 75 mg, 50 mg or 25 mg of rifaximin. In particular embodiments, the quantity of rifaximin is 250 mg. 225 mg. 200 mg, 175 mg, 150 mg, 125 mg, 100 mg. 75 mg, 50 mg or 25 mg of rifaximin. In particular embodiments, the quantity of rifaximin is 175 mg, 150 mg, 125 mg, 100 mg, 75 mg, 50 mg or 25 mg. As noted above, the combination of an antibiotic and a mucolytic agent provides vastly increased therapeutic efficacy, and thus, the amount of the antibiotic can be reduced significantly. Thus, in various embodiments wherein the one or more antibiotic is rifaximin, the quantity of rifaximin is 250 mg. 225 mg, 200 mg, 175 mg, 150 mg, 125 mg, 100 mg, 75 mg, 50 mg or 25 mg. In various embodiments wherein the one or more antibiotic is rifaximin the quantity of rifaximin is 175 mg, 150 mg, 125 mg, 100 mg, 75 mg, 50 mg or 25 mg.

In some embodiments, wherein the GI disease or disorder is SIBO or IBS-D, a method described herein may include administration of about 200 mg of rifaximin and about 600 mg of NAC. In some embodiments, the rifaximin and NAC may be administered in oral unit dosage form (e.g., tablets) and may be combined in one unit dosage or two or more unit dosages (e.g., one tablet or two or more tablets).

In various embodiments, the GI disease or disorder is mixed irritable bowel syndrome (IBS-M).

In various embodiments, the GI disease or disorder is constipation predominant irritable bowel syndrome (IBS-C).

In various embodiments wherein the GI disease or disorder is IBS-C, the one or more antibiotics is rifaximin and neomycin, which may be administered according to a quantity as set forth herein. In various embodiments, the quantity of rifaximin is 550 mg, 500 mg, 400 mg, 350 mg, 300 mg. 275 mg. 250 mg, 225 mg, 200 mg, 175 mg, 150 mg, 125 mg, 100 mg, 75 mg, 50 mg or 25 mg, and the quantity of neomycin is 500 mg, 500 mg, 400 mg, 350 mg, 300 mg, 275 mg, 250 mg. 225 mg. 200 mg, 175 mg, 150 mg, 125 mg, 100 mg, 75 mg, 50 mg or 25 mg. As noted above, the combination of an antibiotic and a mucolytic agent provides vastly increased therapeutic efficacy, and thus, the amount of the antibiotic can be reduced significantly. Thus, in various embodiments wherein the one or more antibiotic is rifaximin and neomycin, the quantity of rifaximin is 250 mg. 225 mg, 200 mg, 175 mg, 150 mg, 125 mg, 100 mg, 75 mg, 50 mg or 25 mg, and quantity of neomycin is 250 mg. 225 mg, 200 mg, 175 mg, 150 mg, 125 mg, 100 mg, 75 mg, 50 mg or 25 mg. In various embodiments wherein the one or more antibiotic is rifaximin and neomycin, the quantity of rifaximin is 175 mg, 150 mg, 125 mg, 100 mg, 75 mg, 50 mg or 25 mg, and quantity of neomycin is 250 mg, 225 mg, 200 mg, 175 mg, 150 mg, 125 mg, 100 mg, 75 mg, 50 mg or 25 mg.

Kits

The invention described herein is also directed to a kit. The kit is useful for practicing the inventive method of treating a GI disease or disorder (e.g., SIBO, IBS), and/or inhibiting the growth of or killing microorganism. The kit is an assemblage of materials or components, including at least one of the inventive compositions. Thus, in some embodiments the kit contains a composition including one or more antibiotics and a mucolytic agent, as described above. In some embodiments, the kit may include one or more antibiotics and a mucolytic agent, as described above.

The exact nature of the components configured in the inventive kit depends on its intended purpose. For example, some embodiments are configured for the purpose of treating a GI disease or disorder; other embodiments are configured for the purpose of inhibiting the growth of or killing microorganism. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treating a GI disease or disorder (e.g., SIBO, IBS), and inhibiting the growth of or killing microorganism. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in treating a GI disease or disorder (e.g., SIBO, IBS), and inhibiting the growth of or killing microorganism. As used herein, the term "package" refers to a suitable solid matrix or material such as glass, plastic, paper, foil, and the like, capable of holding the individual kit components. Thus, for example, a package can be a plastic bottle used to contain suitable quantities of an inventive composition containing one or more antibiotics and a mucolytic agent, or blister pack containing dosages of one or more antibiotics and the mucolytic agent (as one composition or as separate compositions). The packaging material generally has an external label which indicates the contents and/or purpose of the kit and/or its components.

Various embodiments provide for a kit, comprising: a composition comprising one or more antibiotics and a mucolytic agent, and instructions for using the composition.

Various embodiments provide for a kit, comprising one or more antibiotics and a mucolytic agent, and instructions for using the one or more antibiotics and the mucolytic agent.

Examples of antibiotics are as noted above.

In various embodiments, the one or more antibiotics is selected from the group consisting of rifaximin, rifamycin, rifampin, penicillin derivative, fluoroquinolone, macrolide, tetracycline, doxycycline, neomycin, metronidazole and combinations thereof. In various embodiments, wherein the penicillin derivative is ampicillin, the fluoroquinolone is ciprofloxacin, and the macrolide is azithromycin. In various embodiments, the one or more antibiotics is rifaximin. In various embodiments, the one or more antibiotics is rifaximin and neomycin.

In various embodiments, the one or more antibiotic is rifaximin and the composition comprises 550 mg, 500 mg, 400 mg, 350 mg, 300 mg, 275 mg, 250 mg, 225 mg, 200 mg, 175 mg, 150 mg, 125 mg, 100 mg, 75 mg, 50 mg or 25 mg of rifaximin.

As noted above, the inventor believes that the combination of an antibiotic and a mucolytic agent provides vastly increased therapeutic efficacy, and thus, the amount of the antibiotic can be reduced significantly.

Thus, in various embodiments wherein the one or more antibiotic is rifaximin, the kit comprises a composition comprising 250 mg, 225 mg, 200 mg, 175 mg, 150 mg, 125 mg, 100 mg, 75 mg, 50 mg or 25 mg of rifaximin. In various embodiments wherein the one or more antibiotic is rifaximin, the quantity of rifaximin is 175 mg, 150 mg, 125 mg, 100 mg, 75 mg, 50 mg or 25 mg.

In various embodiments wherein the one or more antibiotics is rifaximin and neomycin, the kit comprises a composition comprising 550 mg, 500 mg, 400 mg, 350 mg, 300 mg, 275 mg, 250 mg, 225 mg, 200 mg, 175 mg, 150 mg, 125 mg, 100 mg, 75 mg, 50 mg or 25 mg, and a composition comprising 500 mg, 500 mg, 400 mg, 350 mg, 300 mg. 275 mg, 250 mg, 225 mg, 200 mg, 175 mg, 150 mg, 125 mg, 100 mg, 75 mg, 50 mg or 25 mg. As noted above, the inventor believes that the combination of an antibiotic and a muco- lytic agent provides vastly increased therapeutic efficacy, and thus, the amount of the antibiotic can be reduced significantly. Thus, in various embodiments wherein the one or more antibiotic is rifaximin and neomycin, the quantity of rifaximin is 250 mg. 225 mg. 200 mg, 175 mg, 150 mg, 125 mg, 100 mg, 75 mg, 50 mg or 25 mg. and quantity of neomycin is 250 mg, 225 mg, 200 mg, 175 mg, 150 mg, 125 mg, 100 mg, 75 mg, 50 mg or 25 mg. In various embodi- ments wherein the one or more antibiotic is rifaximin and neomycin, the quantity of rifaximin is 175 mg, 150 mg, 125 mg, 100 mg, 75 mg, 50 mg or 25 mg, and quantity of neomycin is 250 mg. 225 mg. 200 mg, 175 mg, 150 mg, 125 mg, 100 mg, 75 mg, 50 mg or 25 mg. The rifaximin and neomycin can be provided in separate compositions or in one composition.

In various embodiments, the mucolytic agent is selected from the group consisting of dithiothreitol (DTT), N-acetyl cysteine (NAC), acetylcysteine, ambroxol, bromhexine, car- bocisteine, erdosteine, mecysteine, dornase alfa and combi- nations thereof. In various embodiments, the mucolytic agent is dithiothreitol (DTT). In various embodiments, the mucolytic agent is N-acetyl cysteine (NAC).

In embodiments wherein the mucolytic agent is dithio- threitol (DTT), the composition comprises 10-20 v/v % of DTT. In various embodiments wherein the mucolytic agent is dithiothreitol (DTT), the composition comprises 5, 10, 15, 20 or 25 v/v % of DTT. In various embodiments wherein the mucolytic agent is dithiothreitol (DTT), the composition comprises 10, 11, 12, 13, 14, 15, 16, 17, 18, 19 or 20 v/v % of DTT.

In embodiments wherein mucolytic agent is N-acetyl cysteine (NAC), the composition comprises 100-1200 mg of N-acetyl cysteine (NAC). In various embodiments wherein mucolytic agent is N-acetyl cysteine (NAC), the composi- tion comprises 50-100 mg, 100-200 mg, 200-300 mg, 300- 400 mg, 400-500 mg, 500-600 mg, 600-700 mg. 700-800 mg. 800-900 mg. 900-1000 mg, 1000-1100 mg, 1100-1200 mg, 1200-1300 mg, 1300-1400 mg, or 1400-1500 mg of N-acetyl cysteine (NAC) per dose. In various embodiments wherein mucolytic agent is N-acetyl cysteine (NAC), the composition comprises 100, 200, 300, 400, 500, 600, 700, 800, 900, 1000, 1100, or 1200 mg of N-acetyl cysteine (NAC) per dose.

Route of Administration

In various embodiments, the compositions and com- pounds according to the invention may be formulated for delivery via any route of administration. "Route of admin- istration" may refer to any administration pathway known in the art, including but not limited to aerosol, nasal, oral, transmucosal, transdermal or parenteral.

"Transdermal" administration may be accomplished using a topical cream or ointment or by means of a trans- dermal patch.

"Parenteral" refers to a route of administration that is generally associated with injection, including intraorbital, infusion, intraarterial, intracapsular, intracardiac, intrader- mal, intramuscular, intraperitoneal, intrapulmonary, intraspinal, intrasternal, intrathecal, intrauterine, intrave- nous, subarachnoid, subcapsular, subcutaneous, transmu- cosal, or transtracheal. Via the parenteral route, the compo- sitions may be in the form of solutions or suspensions for infusion or for injection, or as lyophilized powders.

Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the par- enteral route, the compositions may be in the form of solutions or suspensions for infusion or for injection.

Via the topical route, the compositions based on com- pounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication.

Via the ocular route, they may be in the form of eye drops.

The compositions according to the invention can also contain any pharmaceutically acceptable carrier. "Pharma- ceutically acceptable carrier" as used herein refers to a pharmaceutically acceptable material, composition, or vehicle that is involved in carrying or transporting a com- pound of interest from one tissue, organ, or portion of the body to another tissue, organ, or portion of the body. For example, the carrier may be a liquid or solid filler, diluent, excipient, solvent, or encapsulating material, or a combina- tion thereof. Each component of the carrier must be "phar- maceutically acceptable" in that it must be compatible with the other ingredients of the formulation. It must also be suitable for use in contact with any tissues or organs with which it may come in contact, meaning that it must not carry a risk of toxicity, irritation, allergic response, immunoge- nicity, or any other complication that excessively outweighs its therapeutic benefits.

The compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The preparations are made following the conventional techniques of pharmacy involving milling, mixing, granu- lation, and compressing, when necessary, for tablet forms; or milling, mixing and filling for hard gelatin capsule forms. When a liquid carrier is used, the preparation will be in the form of a syrup, elixir, emulsion or an aqueous or non- aqueous suspension. Such a liquid formulation may be administered directly p.o. or filled into a soft gelatin capsule.

The compositions according to the invention may be delivered in a therapeutically effective amount. The precise therapeutically effective amount is that amount of the com- position that will yield the most effective results in terms of efficacy of treatment in a given subject. This amount will vary depending upon a variety of factors, including but not limited to the characteristics of the therapeutic: compound (including activity, pharmacokinetics, pharmacodynamics, and bioavailability), the physiological condition of the sub- ject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Thus, in certain embodiments, the invention provides:

1) A composition, comprising:
   (a) one or more antibiotics; and
   (b) a mucolytic agent.
2) The composition of embodiment 1, wherein the one or more antibiotics is selected from the group consisting of rifaximin, rifamycin, rifampin, penicillin derivative, fluoroquinolone, macrolide, tetracycline, doxycycline, neomycin, metronidazole and combinations thereof.
3) The composition of embodiment 2, wherein the penicillin derivative is ampicillin, the fluoroquinolone is ciprofloxacin, and the macrolide is azithromycin.
4) The composition of embodiment 1, wherein the one or more antibiotics is rifaximin.
5) The composition of embodiment 1, wherein the one or more antibiotic is rifaximin and the composition comprises 550 mg, 500 mg, 400 mg, 350 mg, 300 mg, 275 mg, 250 mg, 225 mg, 200 mg, 175 mg, 150 mg, 125 mg, 100 mg, 75 mg, 50 mg or 25 mg of rifaximin.
6) The composition of embodiment 1, wherein the one or more antibiotics is rifaximin and neomycin.
7) The composition of embodiment 1, wherein the mucolytic agent is selected from the group consisting of dithiothreitol (DTT), N-acetyl cysteine (NAC), acetylcysteine, ambroxol, bromhexine, carbocisteine, erdosteine, mecysteine, dornase alfa and combinations thereof.
8) The composition of embodiment 1, wherein the mucolytic agent is dithiothreitol (DTT).
9) The composition of embodiment 1, wherein the mucolytic agent is N-acetyl cysteine (NAC).
10) The composition of embodiment 1, wherein the mucolytic agent is dithiothreitol (DTT) and the composition comprises 10-20 v/v % of DTT.
11) The composition of embodiment 1, wherein the mucolytic agent is N-acetyl cysteine (NAC) and the composition comprises 100-1200 mg of N-acetyl cysteine (NAC).
12) A method of treating a gastrointestinal (GI) disease or disorder, comprising
    (a) administering the composition of embodiment 1, or
    (b) administering one or more antibiotics and administering a mucolytic agent.
13) The method of embodiment 12, comprising administering the composition of embodiment 1.
14) The method of embodiment 12, comprising:
    (a) administering the one or more antibiotics; and
    (b) administering the mucolytic agent.
15) The method of embodiment 12, wherein the GI disease or disorder is small intestinal bacterial overgrowth (SIBO).
16) The method of embodiment 12, wherein the GI disease or disorder is irritable bowel syndrome (IBS).
17) The method of embodiment 12, wherein the GI disease or disorder is diarrhea predominant irritable bowel syndrome (IBS-D).

18) The method of embodiment 12, wherein the GI disease or disorder is mixed irritable bowel syndrome (IBS-M).
19) The method of embodiment 12, wherein the GI disease or disorder is constipation predominant irritable bowel syndrome (IBS-C).
20) The method of embodiment 12, wherein the one or more antibiotics is selected from the group consisting of rifaximin, rifamycin, rifampin, penicillin derivative, fluoroquinolone, macrolide, tetracycline, doxycycline, neomycin, metronidazole and combinations thereof.
21) The method of embodiment 12, wherein the one or more antibiotics is rifaximin.
22) The method of embodiment 12, wherein the one or more antibiotic is rifaximin and the composition comprises 550 mg, 500 mg, 400 mg, 350 mg, 300 mg, 275 mg, 250 mg. 225 mg, 200 mg, 175 mg, 150 mg, 125 mg, 100 mg, 75 mg, 50 mg or 25 mg of rifaximin.
23) The method of embodiment 12, wherein the one or more antibiotics is rifaximin and neomycin.
24) The method of embodiment 12, wherein the mucolytic agent is selected from the group consisting of dithiothreitol (DTT), N-acetyl cysteine (NAC), acetylcysteine, ambroxol, bromhexine, carbocisteine, erdosteine, mecysteine, dornase alfa and combinations thereof.
25) The method of embodiment 12, wherein the mucolytic agent is dithiothreitol (DTT).
26) The method of embodiment 12, wherein the mucolytic agent is N-acetyl cysteine (NAC).
27) The method of embodiment 12, wherein the mucolytic agent is dithiothreitol (DTT) and the composition comprises 10-20 v/v % of DTT.
28) The method of embodiment 12, wherein the mucolytic agent is N-acetyl cysteine (NAC) and the composition comprises 100-1200 mg of N-acetyl cysteine (NAC).
29) A method of inhibiting the growth of or killing microorganisms in one or more regions of a subject's gastrointestinal (GI) system, comprising:
    (a) administering the composition of embodiment 1, or
    (b) administering one or more antibiotics and administering a mucolytic agent.
30) The method of embodiment 29, wherein the one or more regions of the subject's GI system is the small intestines.
31) The method of embodiment 29, comprising administering the composition of embodiment 1.
32) The method of embodiment 29, comprising:
    (a) administering the one or more antibiotics; and
    (b) administering the mucolytic agent.
33) The method of embodiment 29, wherein the one or more antibiotics is selected from the group consisting of rifaximin, rifamycin, rifampin, penicillin derivative, fluoroquinolone, macrolide, tetracycline, doxycycline, neomycin, metronidazole and combinations thereof.
34) The method of embodiment 29, wherein the one or more antibiotics is rifaximin.
35) The method of embodiment 29, wherein the one or more antibiotic is rifaximin and the composition comprises 550 mg, 500 mg, 400 mg, 350 mg, 300 mg, 275 mg, 250 mg, 225 mg, 200 mg, 175 mg, 150 mg, 125 mg, 100 mg, 75 mg, 50 mg or 25 mg of rifaximin.
36) The method of embodiment 29, wherein the one or more antibiotics is rifaximin and neomycin.
37) The method of embodiment 29, wherein the mucolytic agent is selected from the group consisting of dithiothreitol (DTT), N-acetyl cysteine (NAC), acetylcysteine, ambroxol, bromhexine, carbocisteine, erdosteine, mecysteine, dornase alfa and combinations thereof.

38) The method of embodiment 29, wherein the mucolytic agent is dithiothreitol (DTT).

39) The method of embodiment 29, wherein the mucolytic agent is N-acetyl cysteine (NAC).

40) The method of embodiment 29, wherein the mucolytic agent is dithiothreitol (DTT) and the composition comprises 10-20 v/v % of DTT.

41) The method of embodiment 29, wherein the mucolytic agent is N-acetyl cysteine (NAC) and the composition comprises 100-1200 mg of N-acetyl cysteine (NAC).

42) A kit, comprising:
 (a) the composition of embodiment 1, and instructions for using the composition, or
 (b) one or more antibiotics and a mucolytic agent, and instructions for using the one or more antibiotics and the mucolytic agent.

In a particular embodiment, the invention described herein provides a method (i.e., Method 1) of treating a condition, disease or disorder involving a bacterial infection of the gastrointestinal tract, or enhancing the efficacy of a rifamycin (e.g., rifaximin) against a condition, disease or disorder involving a bacterial infection of the gastrointestinal tract, the method comprising administering a therapeutically effective amount of a rifamycin (e.g., rifaximin) and a therapeutically effective amount of a mucolytic agent to a subject in need thereof.

For example, the invention described herein provides for the following embodiments of Method 1:

1.1 Method 1, wherein the rifamycin is selected from rifampicin, rifampin, rifabutin, rifapentine, and rifaximin.

1.2 Method 1, wherein the rifamycin is rifaximin.

1.3 Any preceding method further comprising administering a therapeutically effective amount of a second antibiotic, e.g., selected from neomycin, clarithromycin, tetracycline, sulfamethoxazole, trimethoprim and metronidazole.

1.4 Any of the preceding methods, wherein the rifamycin is administered in an oral dosage of 25-1000 mg once, twice or three times daily.

1.5 Any of the preceding methods, wherein the rifamycin is administered in an oral dosage of 550 mg, 500 mg, 400 mg, 350 mg, 300 mg, 275 mg, 250 mg, 225 mg, 200 mg, 175 mg, 150 mg, 125 mg, 100 mg, 75 mg, 50 mg or 25 mg.

1.6 Any of the preceding methods, wherein the rifamycin is rifaximin administered in an oral dosage of 200 mg three times a day.

1.7 Any of the preceding methods, wherein the duration of treatment is three to fifteen days.

1.8 Any of the preceding methods, wherein the duration of treatment is three days.

1.9 Any of the preceding methods, wherein the duration of treatment is fourteen days.

1.10 Any of the preceding methods wherein the rifamycin is rifaximin administered in an oral dosage of 200 mg two or three times a day for a period of up to fifteen days.

1.11 Any of the preceding methods wherein the rifamycin is rifaximin administered in an oral dosage of 150 mg two or three times a day for a period of up to fifteen days.

1.12 Any of the preceding methods wherein the rifamycin is rifaximin administered in an oral dosage of 100 mg two or three times a day for a period of up to fifteen days.

1.13 Any of the preceding methods, wherein the mucolytic agent is selected from one or more of dithiothreitol (DTT), N-acetyl cysteine (NAC), acetylcysteine, ambroxol, bromhexine, carbocisteine, erdosteine, mecysteine, dornase alfa, thymosin β4, nacystelyn, heparin, dembrexine, guaifenesin, carbocisteine, erdosteine, mecysteine, hyperosmolar saline, mannitol powder, and inhaled surfactants.

1.14 Any of the preceding methods, wherein the mucolytic agent hydrolyzes disulfide bonds that link mucin oligomers.

1.15 Any of the preceding methods wherein the mucolytic agent comprises one or more sulfhydryl groups.

1.16 Any of the preceding methods wherein the mucolytic agent is dithiothreitol (DTT) and/or N-acetyl cysteine (NAC).

1.17 Any of the preceding methods, wherein the mucolytic agent is dithiothreitol (DTT).

1.18 Any of the preceding methods, wherein the mucolytic agent is N-acetyl cysteine (NAC).

1.19 Any of the preceding methods, wherein the mucolytic agent is administered in a dosage amount of about 100-1200 mg.

1.20 Any of the preceding methods, wherein the mucolytic agent and the antibacterial agent are the form of a single composition.

1.21 Any of the preceding methods, wherein the rifamycin and the mucolytic agent are present in separate compositions, which are administered simultaneously to a patient.

1.22 Any of the preceding methods, wherein the rifamycin and the mucolytic agent are present in separate compositions, and wherein the mucolytic agent is administered prior to the rifamycin.

1.23 The preceding method, wherein the mucolytic agent is administered no more than 24 hours prior to the rifamycin.

1.24 The preceding method, wherein the mucolytic agent is administered no more than 12 hours prior to the rifamycin.

1.25 Any of the preceding methods, wherein the condition, disease or disorder mediated by degradation or modulation of mucosal tissue or mucous linings is a bacterial, viral or fungal infection.

1.26 Any of the preceding methods, wherein the condition, disease or disorder mediated by degradation or modulation of mucosal tissue or mucous linings is a bacterial infection.

1.27 Any of the preceding methods, wherein the bacterial infection is a gram-negative bacteria.

1.28 Any of the preceding methods, wherein the bacterial infection is enterotoxigenic *Escherichia coli* (ETEC), enteroaggregative *E. coli, Shigella* spp., *Salmonella* spp., *Campylobacter* spp., *Yersinia* spp., *Vibrio* spp. *Aeromonas* spp., Clostridioides spp., and/or *Plesiomonas* spp.

1.29 Any of the preceding methods wherein the bacterial infection is an *E. coli* infection.

1.30 Any of the preceding methods wherein the bacterial infection is a Clostridioides *difficile* infection.

1.31 Any of the preceding methods, wherein the condition, disease or disorder is an irritable bowel syndrome (IBS) or small intestine bacterial overgrowth (SIBO).

1.32 Any of the preceding methods, wherein the condition, disease or disorder is irritable bowel syndrome (IBS), e.g., diarrhea predominant irritable bowel syndrome (IBS-D), constipation predominant irritable bowel syndrome (IBS-C), or mixed irritable bowel syndrome (IBS-M).

1.33 Any of the preceding methods, wherein the condition, disease or disorder is diarrhea predominant irritable bowel syndrome (IBS-D), 1.34 Any preceding method wherein the condition, disease or disorder is diarrhea predominant irritable bowel syndrome (IBS-D) and following treatment (e.g., following administering a therapeutically effective amount of a rifaximin and a therapeutically effective amount of NAC to the subject), the subject shows an improvement in stool form and reduction in stool frequency from baseline prior to treatment.

1.35 Any preceding method wherein the condition, disease or disorder is diarrhea predominant irritable bowel syndrome (IBS-D) and following treatment (e.g., following administering a therapeutically effective amount of a rifaximin and a therapeutically effective amount of NAC to the subject), the subject shows a decrease in severity of abdominal pain, e.g., as determined from weekly average visual analog scale (VAS) scores, from baseline prior to treatment.

1.36 Any preceding method wherein the condition, disease or disorder is diarrhea predominant irritable bowel syndrome (IBS-D) and following treatment (e.g., following administering a therapeutically effective amount of a rifaximin and a therapeutically effective amount of NAC to the subject), the subject shows a decrease in urgency or bloating, e.g., as determined from weekly average visual analog scale (VAS) scores, from baseline prior to treatment.

1.37 Any preceding method wherein the condition, disease or disorder is diarrhea predominant irritable bowel syndrome (IBS-D) and following treatment (e.g., following administering a therapeutically effective amount of a rifaximin and a therapeutically effective amount of NAC to the subject), the subject shows a reduction of $H_2$ on lactulose hydrogen breath test (LHBT) from baseline prior to treatment.

1.38 Any of the preceding methods, wherein the condition, disease or disorder is small intestine bacterial overgrowth (SIBO).

1.39 Any of the preceding methods, wherein the rifamycin and the mucolytic agent are individually in the form of a tablet or capsule.

1.40 Any of the preceding methods, wherein the rifamycin and the mucolytic agent are individually in the form of a tablet or capsule comprising an enteric coating.

1.41 Any of the preceding methods, wherein the rifamycin and the mucolytic agent are combined in a single tablet or capsule.

1.42 Any of the preceding methods, wherein the rifamycin and the mucolytic agent are combined in a tablet or capsule comprising an enteric coating.

1.43 Any preceding method wherein the rifamycin is rifaximin and the mucolytic agent is DTT.

1.44 Any preceding method wherein the rifamycin is rifaximin and the mucolytic agent is DTT, wherein the rifaximin and DTT are combined in a tablet or capsule.

1.45 Any preceding method wherein the rifamycin is rifaximin and the mucolytic agent is NAC.

1.46 Any preceding method wherein the rifamycin is rifaximin and the mucolytic agent is NAC, wherein the rifaximin and NAC are combined in a tablet or capsule.

1.47 Any preceding method wherein the rifamycin is rifaximin in an amount of 200 mg and the mucolytic agent is NAC in an amount of 600 mg, administered simultaneously, three times daily by mouth, for up to fifteen days.

1.48 Any preceding method wherein the rifamycin and the mucolytic agent are administered as a combination in accordance with any of Combination 1, et seq.

The disclosure further provides a rifamycin and a mucolytic agent for use in combination in a method of treating a condition, disease or disorder involving a bacterial infection of the gastrointestinal tract, e.g., for use in any of Methods 1, et seq.

The disclosure further provides the use of an antibacterial agent and a mucolytic agent in the manufacture of a medicament for use in a method of treating a condition, disease or disorder involving a bacterial infection of the gastrointestinal tract, e.g., a medicament for use in any of Methods 1, et seq.

Accordingly, in various embodiments, the present disclosure also provides for a pharmaceutical combination (i.e., Combination 1) comprising a therapeutically effective amount of a rifamycin and a therapeutically effective amount of a mucolytic agent. For example, the present disclosure provides for the following Combinations:

1.1 Combination 1, wherein the rifamycin is selected from rifampicin, rifampin, rifabutin, rifapentine, or rifaximin.

1.2 Any preceding combination wherein the combination further comprises and effective amount of neomycin, clarithromycin, tetracycline, sulfamethoxazole, trimethoprim, or metronidazole.

1.3 Any of the preceding combinations wherein the rifamycin is rifaximin.

1.4 Any of the preceding combinations, wherein the rifamycin is in an oral unit dosage form comprising 25-1000 mg of the rifamycin in free or salt form.

1.5 Any of the preceding combinations, wherein the rifamycin is in an oral unit dosage form in an amount of 550 mg, 500 mg, 400 mg, 350 mg, 300 mg, 275 mg, 250 mg, 225 mg, 200 mg, 175 mg, 150 mg, 125 mg, 100 mg, 75 mg, 50 mg or 25 mg.

1.6 Any of the preceding combinations, wherein the rifamycin is rifaximin in an oral unit dosage form in an amount of 200 mg.

1.7 Any of the preceding combinations, wherein the rifamycin is rifaximin in an oral unit dosage form in an amount of 550 mg.

1.8 Any of the preceding combinations, wherein the mucolytic agent is selected from one or more of dithiothreitol (DTT), N-acetyl cysteine (NAC), acetylcysteine, ambroxol, bromhexine, carbocisteine, erdosteine, mecysteine, dornase alfa, thymosin β4, nacystelyn, heparin, dembrexine, guaifenesin, carbocisteine, erdosteine, mecysteine, hyperosmolar saline, mannitol powder, and inhaled surfactants.

1.9 Any of the preceding combinations, wherein the mucolytic agent is dithiothreitol (DTT) and/or N-acetyl cysteine (NAC).

1.10 Any of the preceding combinations, wherein the mucolytic agent is dithiothreitol (DTT).

1.11 Any of the preceding combinations, wherein the mucolytic agent is N-acetyl cysteine (NAC).

1.12 Any of the preceding combinations, wherein the mucolytic agent is administered in a dosage amount of about 100-1200 mg.

1.13 Any of the preceding combinations, wherein the mucolytic agent and the rifamycin are the form of a single composition.

1.14 Any of the preceding combinations, wherein the rifamycin and the mucolytic agent are present in separate compositions, which are administered simultaneously to a patient.

1.15 Any of the preceding combinations, wherein the rifamycin and the mucolytic agent are present in separate compositions, and wherein the mucolytic agent is administered prior to the rifamycin.

1.16 The preceding combination, wherein the mucolytic agent is administered no more than 24 hours prior to the rifamycin.

1.17 The preceding combination, wherein the mucolytic agent is administered no more than 12 hours prior to rifamycin.

1.18 Any of the preceding combinations, wherein the combination is for the treatment of an irritable bowel syndrome (IBS) or small intestine bacterial overgrowth (SIBO).

1.19 Any of the preceding combinations, wherein the combination is for use in the treatment of irritable bowel syndrome (IBS).

1.20 Any of the preceding combinations, wherein the combination is for use in the treatment of diarrhea predominant irritable bowel syndrome (IBS-D).

1.21 Any of the preceding combinations, wherein the combination is for use in the treatment of constipation predominant irritable bowel syndrome (IBS-C).

1.22 Any of the preceding combinations, wherein the combination is for use in the treatment of mixed irritable bowel syndrome (IBS-M).

1.23 Any of the preceding combinations, wherein the combination is for use in the treatment of small intestine bacterial overgrowth (SIBO).

1.24 Any of the preceding combinations, wherein the rifamycin and the mucolytic agent are in the form of a tablet or capsule.

1.25 Any of the preceding combinations, wherein the rifamycin and the mucolytic agent are in the form of a tablet or capsule comprising an enteric coating.

1.26 Any of the preceding combination wherein the rifamycin is rifaximin and the mucolytic agent is DTT, and the rifaximin and DTT are combined in a tablet or capsule.

1.27 Any of the preceding combination wherein the rifamycin is rifaximin and the mucolytic agent is NAC, and the rifaximin and NAC are combined in a tablet or capsule.

1.28 Any of the preceding combination wherein the rifamycin is rifaximin in an amount of 200 mg and the mucolytic agent is NAC in an amount of 600 mg, and the rifaximin and NAC are combined in a tablet or capsule.

1.29 Any preceding combination wherein the rifamycin and the mucolytic agent are provided in the form of a kit, with instructions for use.

1.30 Any preceding combination wherein the rifamycin and the mucolytic agent are provided in the form of a kit, with instructions for use, wherein the rifamycin is rifaximin and the mucolytic agent is DTT.

1.31 Any preceding combination wherein the rifamycin and the mucolytic agent are provided in the form of a kit, with instructions for use, wherein the rifamycin is rifaximin and the mucolytic agent is NAC.

1.32 Any preceding combination wherein the rifamycin and the mucolytic agent are provided in the form of a kit, with instructions for use, wherein the rifamycin is rifaximin in oral dosage form comprising 200 mg rifaximin, and the mucolytic agent is NAC in oral dosage form comprising 600 mg NAC.

1.33 Any preceding combinations for use in any of Methods 1, et seq.

The disclosure further provides a pharmaceutical combination according to Combination 1, et. seq., for use in any of Methods 1, et seq.

The disclosure further provides the use of a pharmaceutical combination according to Combination 1, et. seq., in the manufacture of a medicament for use in any of Methods 1.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without (3) Same patient duodenum aspirate sample were vortex and divided in two: (i) Added rifaximin and DTT (Rifaximin dose: 0.01 g/mL); and (ii) Added rifaximin and no DTT (Rifaximin dose: 0.01 g/mL). Culture: MacConkey aerobically and blood agar anaerobically. Again, DTT improved rifaximin dissolution The sample without DTT, rifaximin could not penetrate on mucus. Results in Tables 1a and 1b below.

(4) Same patient duodenum aspirate sample were vortex and divided in two: (i) Added rifaximin and DTT (Rifaximin dose: 0.1 g/mL); and (ii) Added rifaximin and no DTT (Rifaximin dose: 0.1 g/mL). Culture: MacConkey aerobically and blood agar anaerobically. DTT improved rifaximin dissolution. The sample without DTT, rifaximin could not penetrate on mucus. Results in Tables 1a and 1b below.

TABLE 1a

| | Before Rifaximin | | | | | | | |
| | Experiment # | | | | | | | |
| | 1 | | 2 | | 3 | | 4 | |
| | No DTT | With DTT | No DTT | With DTT | No DTT | With DTT | No DTT | With DTT |
| Blood agar (CFU/mL) | 6800 | 72000 | too high all Dilution | too high all Dilution | 72000 | 60000 | 250000 | 1600000 |
| MacConkey agar (CFU/mL) | 4600 | 4800 | 338000 | 338000 | 40 | 20 | 0 | 0 |

TABLE 1b

| | Rifaximin treatment | | | | | | | |
| | Experiment # | | | | | | | |
| | 1 | | 2 | | 3 | | 4 | |
| | No DTT | With DTT | No DTT | With DTT | No DTT | With DTT | No DTT | With DTT |
| Blood agar (CFU/mL) | 6000 | 0 | too high all Dilution | 536000 | 800 | 40 | 16000 | 0 |
| MacConkey agar (CFU/mL) | 4000 | 0 | 343000 | 388000 | 40 | 0 | 0 | 0 | the exercise of inventive capacity and without departing from the scope of the invention.

Example 1

(1) Same patient duodenum aspirate sample were vortex and divided in two: (i) Added rifaximin and DTT (Rifaximin dose: 0.01 g/mL); (ii) Added rifaximin and no DTT (Rifaximin dose: 0.01 g/mL). Culture: blood agar and MacConkey aerobically, and blood agar anaerobically. The sample with DTT was observed to improved rifaximin dissolution. The sample without DTT, rifaximin could not penetrate on mucus. Results in Tables 1a and 1b below.

(2) Same patient duodenum aspirate sample were vortex and divided in two: (i) Added rifaximin and DTT (Rifaximin dose: 0.1 g/mL); and (ii) Added rifaximin and no DTT (Rifaximin dose: 0.1 g/mL). Culture: MacConkey aerobically and blood agar anaerobically. Sample with DTT was observed to improved rifaximin dissolution. Results in Tables 1a and 1b below.

The results show that DTT improved rifaximin dissolution. Aspirate samples treated with DTT and Rifaximin together showed decreased bacterial CFU/mL when compared to Rifaximin alone. DTT also improved Rifaximin's effect against anaerobes in all experiments. Rifaximin plus DTT improvement against Gram-negative is species specific (experiment #1 and #3 showed effectiveness. Experiment #2: no effectiveness).

Example 2—Evaluation of the Efficacy and Safety of Rifaximin in Combination with N-Acetylcysteine (NAC) in Adult Patients with Irritable Bowel Syndrome with Diarrhea The objectives and endpoints of this study are summarized as follows:

| OBJECTIVES | ENDPOINTS | JUSTIFICATION FOR ENDPOINTS |
|---|---|---|
| Primary | | |
| To assess the efficacy of combined Rifaximin and NAC therapy vs. Rifaximin alone in decreasing clinical symptoms in subjects with IBS-D. | 1. Improvement in stool form and reduction in stool frequency from baseline, as determined from stool diary data comparing rifaximin alone vs rifaximin and NAC<br>2. Decrease in severity of abdominal pain, as determined from weekly average visual analog scale (VAS) scores, relative to rifaximin alone. | These endpoints were chosen as they align with the endpoints chosen to assess rifaximin efficacy in the Target 1 & 2 trials. |
| Secondary | | |
| To determine the optimal dosage of Rifaximin for use in combination with NAC to decrease clinical symptoms in subjects with IBS-D. | 1. Improvement in urgency, as determined from weekly average VAS scores, relative to rifaximin alone<br>2. Improvement in bloating, as determined from weekly average VAS scores, relative to rifaximin alone<br>3. Reduction of $H_2$ on lactulose hydrogen breath test (LHBT) from baseline, relative to rifaximin alone | These endpoints were chosen as they align with the endpoints chosen to assess rifaximin efficacy in the Target 1 & 2 trials. |
| Tertiary/Exploratory | | |
| To determine the effects of rifaximin in combination with NAC on the gut microbiome | 1. Changes in microbiome profiles from baseline, as determined by 16S rRNA gene sequencing | Rifaximin has been shown to have minimal effects on the gut microbiome. In this study, we will determine the effects of combining rifaximin with NAC on the gut microbiome, using stool samples |
| To determine whether artificial intelligence characterization of Bristol stool scores (via the Dieta App) for stool photos can be used to normalize stool scores | 2. Normalization of stool scores | Subjective interpretation of stool scores is a challenge for studies. In this study, we will test whether using the novel Dieta App to characterize Bristol stool scores for stool photos can reduce this subjectivity and normalize stool scores |

The study is a prospective proof-of-concept double-blind (to dose of NAC) clinical trial to determine the efficacy of combined rifaximin and NAC therapy vs. rifaximin alone in decreasing clinical symptoms in subjects with IBS-D.

The study is a single-site, open-label trial which consists of 3 phases:

Run-In Phase: Eligible subjects with IBS-D who consent to participate are recruited. After provision of informed written consent, these subjects undergo baseline testing as described in the Schedule of Activities and complete a daily stool diary for 14 days as well as weekly symptom questionnaires.

Treatment Phase: Subjects are randomized in to one of 3 study arms and receive either:

Rifaximin 550 mg by mouth three times daily for 14 days, OR

Rifaximin 200 mg plus placebo by mouth three times daily for 14 days,

OR

Rifaximin 200 mg plus N-acetylcysteine (600 mg) by mouth three times daily for 14 days.

Subjects complete a daily stool diary for 14 days of treatment as well as weekly symptom questionnaires.

Follow-Up Phase: Upon completion of treatment, subjects undergo repeat testing as at baseline. Subjects then complete a daily stool diary for 28 days as well as weekly symptom questionnaires. At the end of this phase, subject complete an end-of-study visit with additional repeat testing as described in the Schedule of Activities.

The inclusion criteria for this study are as follows:

Male or female subjects aged 18-75 years old inclusive

Meet Rome III criteria for IBS-D and, in order to progress to treatment phase, meet the following:

An average score of greater than or equal to 3 for IBS-related abdominal pain. Abdominal pain scores were based on subject response to the following daily question: "In regards to your specific IBS symptom of abdominal pain, on a scale of 0-10, what was your worst IBS-related abdominal pain over the last 24 hours? 'Zero' means you have no pain at all; 'Ten' means the worst possible pain you can imagine."

An average score of greater than or equal to 3 for IBS-related bloating. Bloating scores were based on subject response to the following daily question: "In regards to your specific IBS symptom of bloating, on a scale of 0-6, how bothersome was your IBS-related bloating in the last 24 hours? 0=not at all; 1=hardly; 2=somewhat; 3=moderately; 4=a good deal; 5=a great deal; 6=a very great deal."

At least 2 days in a week with stool consistency of 6 (fluffy pieces with ragged edges, a mushy stool) or 7 (watery stool, no solid pieces; entirely liquid) using the Bristol Stool-Form Scale (BSS). Stools using the BSS were scored as follows: 1=Separate hard lumps, like nuts (hard to pass); 2=Sausage-shaped but lumpy; 3=Like a sausage but with cracks on its surface; 4=Like a sausage or snake, smooth and soft; 5=Soft blobs with clear cut edges (passed easily); 6=Fluffy pieces with ragged edges, a mushy stool; 7=Watery stool, no solid pieces; entirely liquid.

Colonoscopy must have been completed within the past 10 years

Subjects are capable of understanding the requirements of the study, are willing to comply with all the study procedures, and are willing to attend all study visits.

Agree to use an acceptable method of contraception throughout their participation in the study. Acceptable methods of contraception include:

double barrier methods (condom with spermicidal jelly or a diaphragm with spermicide), hormonal methods (e.g. oral contraceptives, patches or medroxyprogesterone acetate), an intrauterine device (IUD) with a documented failure rate of less than 1% per year.

Abstinence or partner(s) with a vasectomy may be considered an acceptable method of contraception at the discretion of the investigator.

Female subjects who have been surgically sterilized (e.g. hysterectomy or bilateral tubal ligation) or who are postmenopausal (total cessation of menses for >1 year) will not be considered "females of childbearing potential".

All subjects will provide Institutional Review Board (IRB)-approved informed written consent prior to beginning any study-related activities.

The exclusion criteria are as follows:

Prior use of rifaximin to treat IBS symptoms

Use of any oral antibiotics in the last two months

Subjects with history of intestinal surgery (except appendectomy or cholecystectomy) Subjects with known pelvic floor dysfunction Pregnancy Nursing mothers Poorly controlled/uncontrolled significant medical condition that would interfere with study procedures History of bowel obstruction History of inflammatory bowel disease or celiac disease History of HIV Cirrhosis IBS-C/chronic idiopathic constipation Poorly controlled diabetes or thyroid disease History of anorectal radiation/surgery History of prostatitis Known allergy or hypersensitivity to rifaximin, rifamycin or NAC Current treatment with eluxadoline or opiates Current treatment with warfarin or cyclosporine Development of any of the exclusion criteria during the study is a basis for subject discontinuation.

Demographics and medical history: The study staff record the subject's sex, date of birth, and ethnic origin. Medical history (e.g., previous diagnoses, diseases or surgeries) will be collected. Findings are recorded in REDCap via the medical history questionnaire. Concomitant medications are also b reviewed Physical exam including vital signs: Complete physical exams are performed by the principal investigator or a physician co-investigator. The general examination includes evaluation of the head, cars, eyes, nose, throat, endocrine, cardiovascular, respiratory, abdomen, skin, neurological, extremities, and musculoskeletal systems. Vital sign measurements, including height, body weight, blood pressure, radial pulse rate, respiratory rate, and temperature will be recorded after the subject has been semi-supine for at least five minutes prior to the test. Abnormalities noted at baseline (Visit 1) are recorded as medical history. Any clinically significant change from baseline are recorded as an adverse event.

Urine pregnancy test: Subjects who are women of childbearing potential are asked to provide a urine sample for pregnancy testing. Pregnancy is considered an Exclusion Criterion.

Lactulose breath test: Subjects are asked to undergo a 24-hour preparatory period just prior to the test. Subjects maintain a bland diet during the first 12 hours and fast during the remaining 12. A baseline breath sample is collected by exhaling into disposable collection bag with a volume of 750 mL. Subjects then consume 10 g lactulose dissolved in water. Subsequent breath samples are collected every 15 minutes over the remainder of the 120-minute test. Breath samples are analyzed for hydrogen, methane, carbon dioxide, and hydrogen sulfide levels immediately after collection via gas chromatograph.

Clinical Symptom Questionnaires (VAS): A baseline symptom questionnaire is completed. Symptom severity is recorded using a visual analog scale (VAS) on a scale of 0 (no symptom) to 100 (maximum symptom). This either is filled online using a secure, web-based application for building and managing online surveys and databases, or is completed in paper format.

Blood draw: Blood is drawn by a trained research nurse and collected for complete blood count (CBC), complete metabolic panel (CMP), erythrocyte sedimentation rate (ESR), and, in women of childbearing potential, for serum pregnancy testing. Laboratory analyses is performed in a central clinical laboratory. Reference ranges are supplied by the clinical laboratory and used by the investigator to assess the laboratory results for clinical significance and pathological changes. An additional blood sample is drawn for exploratory cytokines.

Stool collection (optional): At the end of the study visit, subjects are provided with a stool collection kit and asked to obtain a stool sample on the day prior to their next visit. Subjects are instructed to store the sample in the refrigerator and to return it to study staff on their visit the following day. The provision of a stool sample is optional and is used for exploratory analyses of the effects of combined rifaximin and NAC on the gut microbiome.

Daily stool diary: Subjects are asked to complete a daily stool diary at home, using the Bristol Stool Chart as a visual aid, either online or in paper format. Subjects are also asked to use the Dieta mobile application, which includes a stool image capture feature and computer vision technology that objectively classifies stool consistency.

For both rifaximin and NAC, there are no expected adverse effects. While there are side effects that occur in more than 1% of subjects, these are not more common than placebo in the case of rifaximin based on previous clinical trials. As such, these side effects are not "expected". Adverse events are tracked and reported.

Improvements in primary, secondary and tertiary endpoints as defined above are assessed and reported.

Upon completion of this study, it is expected that the combination of rifaximin and NAC will demonstrate that NAC increases the activity of rifaximin as compared to rifaximin therapy alone for decreasing clinical symptoms in subjects with IBS-D.

What is claimed is:

1. A method of treating diarrhea predominant irritable bowel syndrome (IBS-D) in a subject in need thereof, the method comprising orally administering a therapeutically effective amount of rifaximin and a therapeutically effective amount of N-acetyl cysteine (NAC) to the subject.

2. The method of claim 1, wherein the rifaximin is administered in an oral dosage of 25-1000 mg.

3. The method of claim 1, wherein the rifaximin is administered in an oral dosage of 200 mg.

4. The method of claim 1, wherein the duration of treatment is three to fifteen days.

5. The method of claim 1, wherein the rifaximin is in an amount of 200 mg and the NAC is in an amount of 600 mg.

6. The method of claim 1, wherein the NAC is in an amount of about 100-1200 mg.

7. The method of claim 1, wherein the therapeutically effective amount of rifaximin and the therapeutically effective amount of N-acetyl cysteine (NAC) are provided in the form of a tablet or capsule comprising an enteric coating.

8. The method of claim 1, wherein the NAC and the rifaximin are in a single composition.

9. The method of claim 1, wherein the NAC and the rifaximin are present in separate compositions, which are administered simultaneously to the subject.

10. The method of claim 1, wherein the NAC and the rifaximin are present in separate compositions, which are administered sequentially.

11. The method of claim 1, wherein the NAC is administered prior to the rifaximin.

12. A method of treating diarrhea predominant irritable bowel syndrome (IBS-D) in a subject in need thereof, comprising orally administering a therapeutically effective amount of rifaximin and a therapeutically effective amount of N-acetyl cysteine (NAC) to the subject, wherein the rifaximin is administered in an amount of 200 mg and the NAC is administered in an amount of 600 mg, thereby treating the IBS-D in the subject.

\* \* \* \* \*